US00PP23830P3

(12) United States Plant Patent
Danziger

(10) Patent No.: US PP23,830 P3
(45) Date of Patent: Aug. 13, 2013

(54) *BRACHYCOME* PLANT NAMED 'DBRASC9'

(50) Latin Name: ***Brachycome* hybrid**
Varietal Denomination: DBRASC9

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 110 days.

(21) Appl. No.: 13/134,072

(22) Filed: May 27, 2011

(65) Prior Publication Data

US 2012/0304351 P1 Nov. 29, 2012

(51) Int. Cl.
*A01H 5/00* (2006.01)

(52) U.S. Cl.
USPC ..... Plt./411

(58) Field of Classification Search
USPC ..... Plt./411
See application file for complete search history.

*Primary Examiner* — June Hwu
(74) *Attorney, Agent, or Firm* — Cassandra Bright

(57) ABSTRACT

A new and distinct *Brachycome* cultivar named 'DBRASC9' is disclosed, characterized by abundant flowering and violet flower color. The new variety has a compact growth habit, prolific branching and small to medium sized foliage. The new variety is a *Brachycome*, normally produced as an outdoor garden or container plant.

2 Drawing Sheets

Figure 1:
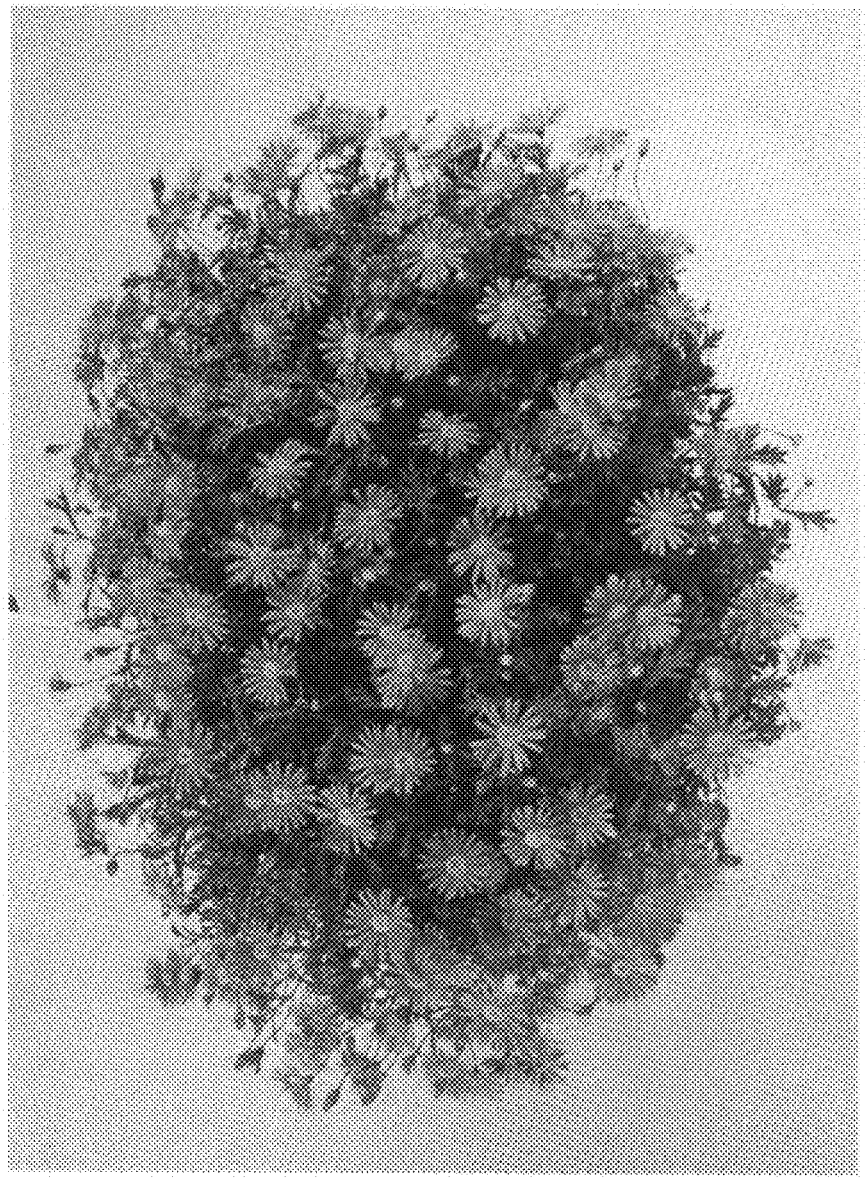

Latin name of the genus and species: *Brachycome* hybrid.
Variety denomination: 'DBRASC9'.

BACKGROUND OF THE INVENTION

The new *Brachycome* cultivar is a product of a planned breeding program conducted by the inventor, Gavriel Danziger, in Moshav Mishmar Hashiva, Israel. The objective of the breeding program was to produce new *Brachycome* varieties for ornamental commercial applications. The cross resulting in this new variety was made during April 2008.

The seed parent is the unpatented, proprietary seedling variety referred to as *Brachycome* hybrid 'PT-8-441' The pollen parent is unknown, as the crossing resulting in 'DBRASC9' was an open pollination, with unidentifiable pollen parents. The new variety was discovered in May 2009 by the inventor in a group of seedlings resulting from the 2008 crossing, in a research greenhouse in Moshav Mishmar Hashiva, Israel.

Asexual reproduction of the new cultivar 'DBRASC9' by vegetative cuttings was first performed at a research greenhouse in Moshav Mishmar Hashiva, Israel in June 2009 and has shown that the unique features of this cultivar are stable and reproduced true to type in successive generations.

SUMMARY OF THE INVENTION

The cultivar 'DBRASC9' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DBRASC9' These characteristics in combination distinguish 'DBRASC9' as a new and distinct *Brachycome* cultivar:

1. Highly floriferous
2. Mounded plant habit
3. Large violet colored flowers

4. Small to medium foliage size
5. Prolific branching

Plants of the new cultivar 'DBRASC9' are similar to plants of the seed parent, *Brachycome* hybrid 'PT-8-441' in most horticultural characteristics, however, plants of the new cultivar 'DBRASC9' have a more compact plant habit, and more flowers per plant. Additionally, the new cultivar begins flowering earlier and produces more lateral branches than the seed parent.

COMMERCIAL COMPARISON

Plants of the new cultivar 'DBRASC9' are comparable to the commercial variety *Brachycome* 'Strawberry Mousse' U.S. Plant Pat. No. 10,194. These *Brachycome* varieties are similar in most horticultural characteristics. The new variety 'DBRASC9' differs in having smaller flowers, more flowers, lighter green foliage and a more mounded, dense plant form than 'Strawberry Mousse'. Additionally, the new variety has smaller foliage and a more violet than pink flower color.

Plants of the new cultivar 'DBRASC9' are comparable to the commercial variety *Brachycome* 'Bonrapi' U.S. Plant Pat. No. 21,627. The new variety 'DBRASC9' differs in having smaller flowers, more flowers lighter green foliage and a more mounded, dense plant form than 'Bonrapi'. Additionally, the new variety has a more violet than pink flower color.

BRIEF DESCRIPTION OF THE PHOTOGRAPHS

The accompanying photograph in FIG. 1 illustrates in full color a typical plant of 'DBRASC9' grown in a greenhouse, in a 13 cm basket. Age of the plant photographed is approximately 3 months from a rooted cutting.

Figure 2:
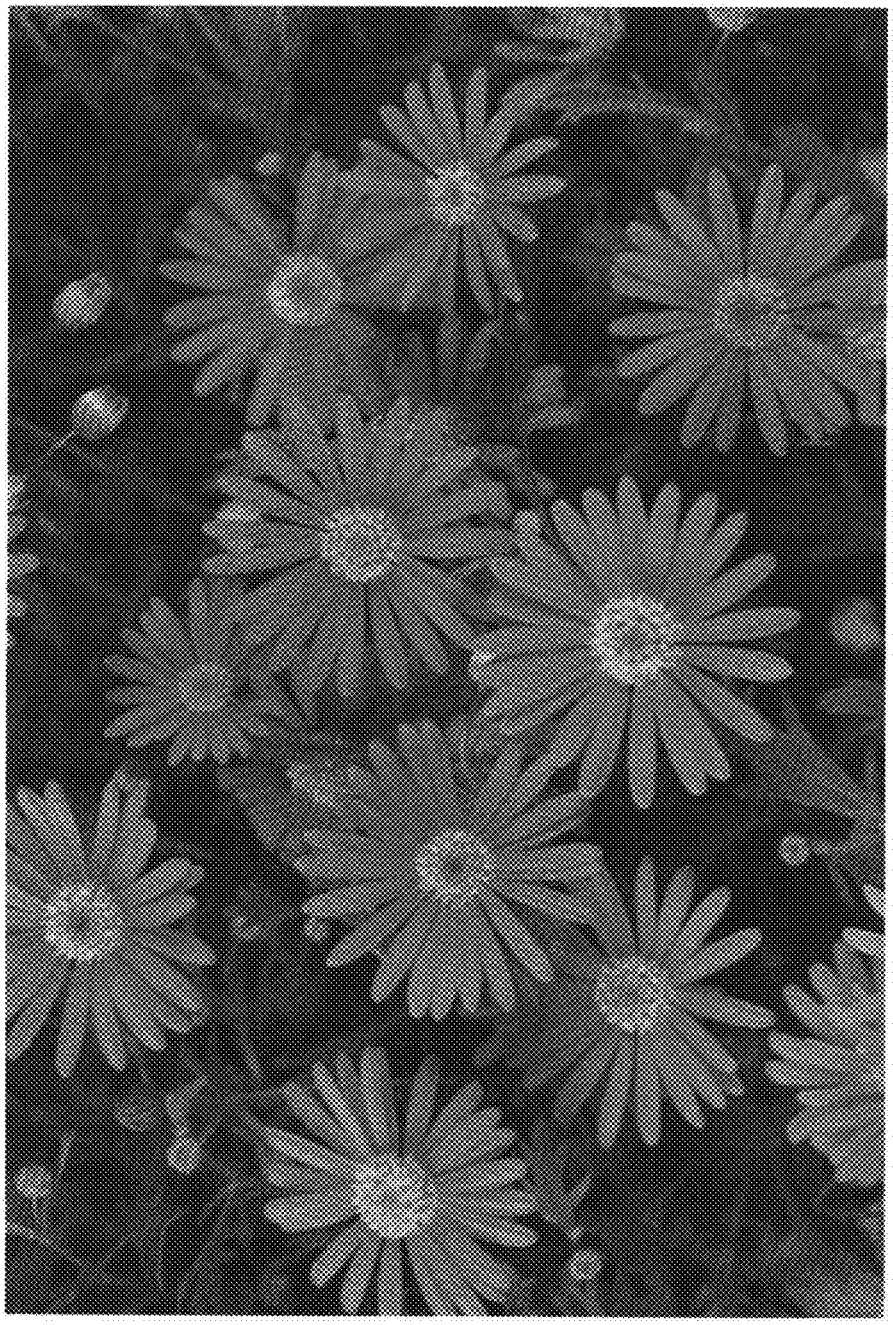

FIG. 2 illustrates in full color a close up of a typical bloom of 'DBRASC9'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DBRASC9' plants grown in a greenhouse during Spring in Gilroy, Calif. The growing temperature ranged from 13° C. to 26° C. during the day and from 13° C. to 18° C. during the night. General light conditions are bright, normal sunlight. Measurements and numerical values represent averages of typical plant types.

Botanical classification: *Brachycome* hybrid 'DBRASC9'.

PROPAGATION

Time to initiate roots: 24 days at approximately 20° C.
Root description: Fibrous, fine.

PLANT

Growth habit: Mounded, compact.
Height: Approximately 20 cm.
Plant spread: Approximately 40 cm.
Growth rate: Medium.
Branching characteristics: Very free branching.
Length of lateral branches: Approximately 20 cm.
Diameter of lateral branches: Approximately 0.1 cm.
Texture of lateral branches: Glabrous.
Internode length: Approximately 1.5 cm.
Strength of stem: Strong.
Color of lateral branches: Near RHS Green 137 B.
Aspect/angle of branches: Semi upright.
Number of leaves per lateral branch: Approximately 15.

FOLIAGE

Leaf:
- *Arrangement*.—Alternate.
- *Average length*.—Approximately 4 cm.
- *Average width*.—Approximately 2.5 cm.
- *Shape of blade*.—Spatulate.
- *Apex*.—Acute.
- *Base*.—Cuneate.
- *Attachment*.—Sessile.
- *Margin*.—Pinnatifid.
- *Texture of top surface*.—Glabrous.
- *Texture of bottom surface*.—Glabrous.
- *Appearance top surface*.—Shiny.
- *Appearance bottom surface*.—Shiny.
- *Color*.—Young foliage upper side: Near RHS Yellow-Green 147 A. Young foliage under side: Near RHS Yellow-Green 147 B. Mature foliage upper side: Near RHS Green 137 A. Mature foliage under side: Near RHS Green 137 C.
- *Venation*.—Type: Pinnate. Venation color upper side: Near RHS Green 137 C. Venation color under side: Near RHS Green 137 C.

Petiole: Not present.
Bloom period: All year round when grown in the greenhouse, Spring through Summer outdoors.
Bud:
- *Bud shape*.—Ovoid.
- *Bud length*.—Approximately 1 cm.
- *Bud diameter*.—Approximately 0.5 cm.
- *Bud color*.—Near RHS Purple-Violet N 81B.

Inflorescence:
- *Form*.—Capitulum.

Flower:
- *Diameter of entire flower*.—Approximately 3.5 cm.
- *Depth of flower*.—Approximately 1 cm.
- *Width of disc*.—Approximately 1 cm.
- *Depth of disc*.—Approximately 0.5 cm.

Ray florets:
- *Number of ray florets*.—Avg. 26.
- *Length*.—Approximately 1.2 cm.
- *Width*.—Approximately 0.2 cm.
- *Apex shape*.—Obtuse.
- *Margin*.—Entire.
- *Upper surface texture*.—Smooth.
- *Lower surface texture*.—Smooth.

Color:
- *Ray florets*.—Upper surface at first opening: Near RHS Violet N 87 A. Upper surface at maturity: Near RHS Violet N 87 A. Upper surface at fading: Near RHS Violet N 87 C. Under surface at first opening: Near RHS Violet N 87 D. Under surface at maturity: Near RHS Violet N 87 D. Under surface at fading: Near RHS Violet N 87 D.
- *Disc florets*.—Number of Disc Florets: about 35. Length: Approximately 0.4 cm. Width: Approximately 0.1 cm. Shape: Tubular. Margin: Entire.
- *Color*.—At first opening: Near RHS Yellow-Green N 144 B. At maturity: Near RHS Yellow 5 B. At fading: Near RHS Yellow 5 C.

Fragrance: None.

PHYLLARIES/INVOLUCRAL BRACTS

Number: Approximately 14.
Sepal length: Approximately 0.3 cm.
Sepal width: Approximately 0.6 cm.
Sepal texture: Glabrous.
Apex shape: Acute.
Margin: Entire.
Color: Near RHS Green 137 A.
Peduncle:
- *Peduncle length*.—Approximately 5 cm.
- *Peduncle diameter*.—Approximately 0.1 cm.
- *Angle*.—Approximately 45 deg from center of whorl.
- *Color*.—Near RHS Yellow-Green 146A.
- *Peduncle texture*.—Glabrous.

REPRODUCTIVE ORGANS

Disc florets:
- *Androecium*.—Stamens: 5. Anther shape: Linear. Anther length: Approximately 0.1 cm. Anther color: Near RHS Yellow 5 B. Pollen quantity: Moderate.
- *Gynoecium*.—Pistil number: 1. Pistil shape: Linear. Pistil length: Approx 0.4 cm. Style length: Approx 0.1 cm. Style color: Near RHS Yellow-Green N144 B. Stigma shape: Bilobate. Stigma color: Near RHS Yellow-Green 151 A. Ovary diameter: about 0.1 cm. Ovary color: Near RHS Yellow-Green 151 D.

Ray florets:
- *Androecium*.—Not present.
- *Gynoecium*.—Pistil number: 1. Pistil shape: Linear. Pistil length: Approx. 0.4 cm. Style length: Approx. 0.1 cm. Style color: Near RHS Yellow-Green N144 B. Stigma shape: Bilobate. Stigma color: Near RHS Yellow-Green 151 A. Ovary diameter: about 0.1 cm. Ovary color: Near RHS Yellow-Green 151 D.

OTHER CHARACTERISTICS

Seeds and fruits: Not observed.

Disease/pest resistance: Neither resistance nor susceptibility to diseases or insects has been observed.

Temperature tolerance: Temperature tolerance from approximately −3° to at least 40° C.

What is claimed is:

1. A new and distinct cultivar of *Brachycome* plant named 'DBRASC9' as herein illustrated and described.

* * * * *